(12) United States Patent
Brianza et al.

(10) Patent No.: US 9,603,670 B2
(45) Date of Patent: Mar. 28, 2017

(54) METHOD FOR DESIGNING AND/OR OPTIMIZING A SURGICAL DEVICE

(75) Inventors: Stefano Brianza, Davos Dorf (CH); Damiano Schiuma, Davos Platz (CH); Andrea Tami, Davos Platz (CH)

(73) Assignee: AO Technology AG, Chur (CH)

( * ) Notice: Subject to any disclaimer, the term of this patent is extended or adjusted under 35 U.S.C. 154(b) by 582 days.

(21) Appl. No.: 13/581,029

(22) PCT Filed: Feb. 25, 2010

(86) PCT No.: PCT/CH2010/000046
§ 371 (c)(1),
(2), (4) Date: Sep. 7, 2012

(87) PCT Pub. No.: WO2011/103689
PCT Pub. Date: Sep. 1, 2011

(65) Prior Publication Data
US 2012/0323282 A1 Dec. 20, 2012

(51) Int. Cl.
*A61B 17/80* (2006.01)
*A61B 34/10* (2016.01)
(Continued)

(52) U.S. Cl.
CPC .......... *A61B 34/10* (2016.02); *A61B 17/1728* (2013.01); *A61B 17/72* (2013.01); *A61B 17/8052* (2013.01);
(Continued)

(58) Field of Classification Search
CPC .............. A61B 19/50; A61B 2019/501; A61B 2019/502; A61B 2019/505;
(Continued)

(56) References Cited

U.S. PATENT DOCUMENTS 4,704,686 A 11/1987 Aldinger
5,452,407 A 9/1995 Crook
(Continued)

FOREIGN PATENT DOCUMENTS

EP 1 430 852 A2 6/2004

OTHER PUBLICATIONS

The International Preliminary Report on Patentability, dated Aug. 28, 2012 in corresponding International Patent Application No. PCT/CH2010/000046, filed Feb. 25, 2010.

*Primary Examiner* — Kevin T Truong
*Assistant Examiner* — Tracy Kamikawa
(74) *Attorney, Agent, or Firm* — Rankin, Hill & Clark LLP

(57) ABSTRACT

A method for designing and/or optimizing an implant that has one or more through holes with a central axis for receiving a bone fixation element. The method includes: providing a general collection of three-dimensional bone quality data obtained from a patient population; identifying in the patient population N>2 categories of patients with significantly different N>2 homologous sub-collections of bone quality data; and designing an implant or optimizing an existing implant for each of the N>2 sub-collections such that the at least one through hole is located at an optimal place and with an optimal direction of the central axis relative to the implant. The optimal position and direction is chosen based on each of the N>2 sub-collections of data so as to obtain an optimal anchorage of the bone fixation element in the bone when introduced through the through hole.

20 Claims, 3 Drawing Sheets

(51) Int. Cl.
*A61B 17/17* (2006.01)
*A61B 17/72* (2006.01)

(52) U.S. Cl.
CPC ..... *A61B 17/8061* (2013.01); *A61B 2034/108* (2016.02)

(58) Field of Classification Search
CPC ........ A61B 2019/507; A61B 2019/508; A61B 6/032; A61B 17/7059; A61B 17/80; A61B 17/8004; A61B 17/8014; A61B 17/8019; A61B 17/8023; A61B 17/8033; A61B 17/8042; A61B 17/8047; A61B 17/8052; A61B 17/8061
USPC .................................................. 606/280, 286
See application file for complete search history.

(56) References Cited

U.S. PATENT DOCUMENTS

| | | | |
|---|---|---|---|
| 2005/0240187 A1* | 10/2005 | Huebner et al. | 606/69 |
| 2007/0238969 A1* | 10/2007 | Song et al. | 600/410 |
| 2008/0234833 A1 | 9/2008 | Bandoh et al. | |
| 2008/0287954 A1* | 11/2008 | Kunz et al. | 606/87 |
| 2009/0089034 A1* | 4/2009 | Penney et al. | 703/11 |
| 2010/0057138 A1* | 3/2010 | Murner et al. | 606/308 |
| 2011/0060373 A1* | 3/2011 | Russell et al. | 606/304 |

* cited by examiner

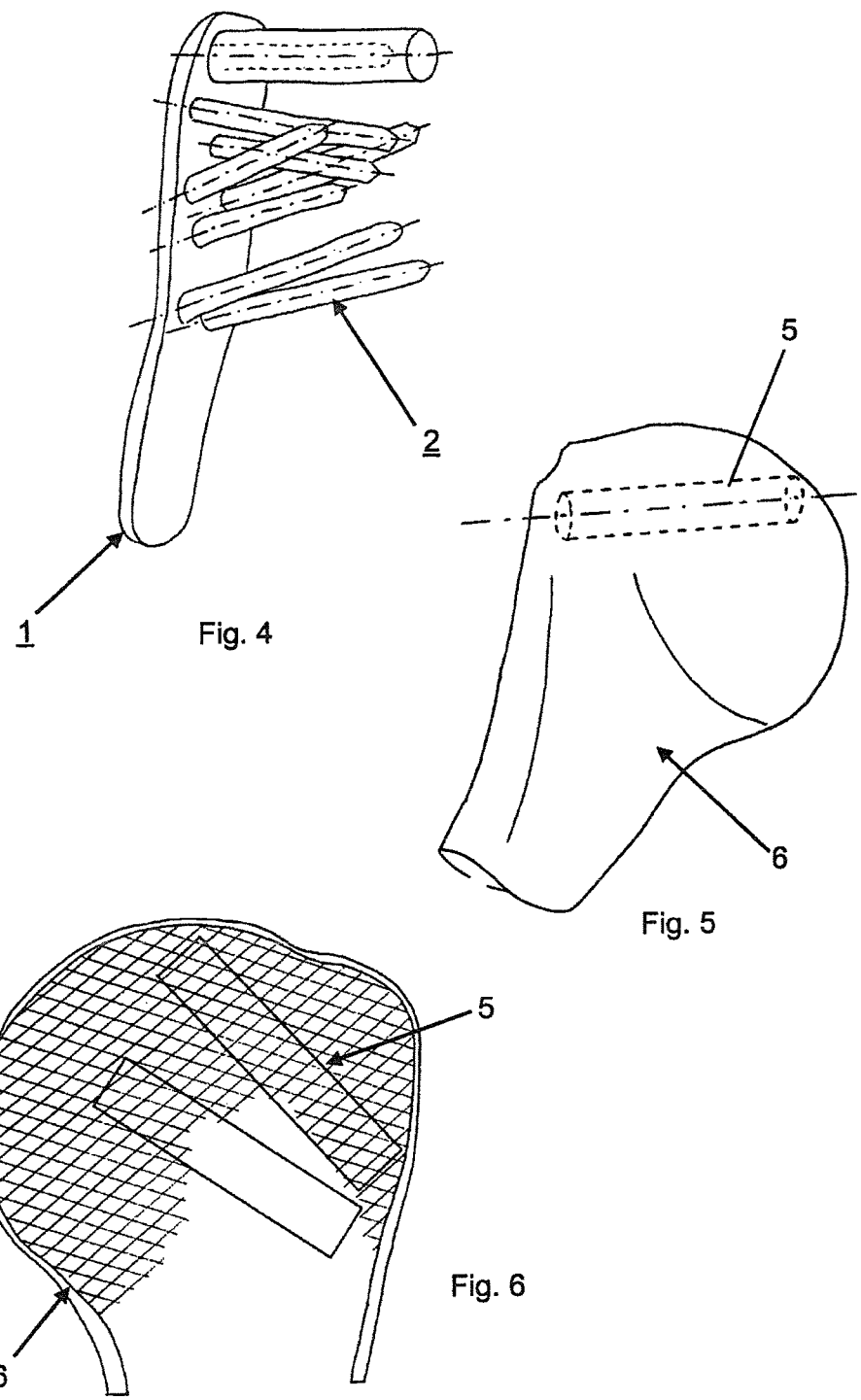

METHOD FOR DESIGNING AND/OR OPTIMIZING A SURGICAL DEVICE

BACKGROUND OF THE INVENTION

1. Field of the Invention

The invention relates to a method for designing and/or optimizing a surgical device, to a method for manufacturing a surgical device, in particular an implant, to an implant manufactured by using said method, and to a method for fixing bones using said implant.

2. Description of the Related Art

Today surgical implants for fixation at or in a bone by means of bone fixation elements (e.g. screw or bolts) are manufactured taking into account the following parameters only
a) anatomical shape of the bone to or in which the implant is to be fixed;
b) type of fracture most frequently encountered; and
c) size of the patient.

No consideration is paid to the following parameters which are of even more importance than the above mentioned:
d) quality of the bone to or in which the implant is to be fixed (e.g. density, porosity, orientation of trabeculi and lamellae, distribution of cortex/spongiosa);
e) variation of these bone qualities depending on the specific patient (e.g. age, sex, race, size, health); and
f) post-operative loading conditions.

For the above reasons present designs of surgical implants, in particular of bone plates and intramedullary nails are mainly oriented to fracture typology and not to specific needs of a category of patients.

Thus, there remains a need for an improved method of design and manufacture of surgical implants for fixation at or in a bone by means of bone fixation elements.

It is an object of the invention to provide an improved method of design and manufacture of surgical implants for fixation at or in a bone by means of bone fixation elements which is more patient oriented, i.e. which takes into consideration additional relevant and critical bone parameters better defining each patient category.

The invention solves the posed problem with a method for designing and/or optimizing a surgical device as claimed, with a method for manufacturing a surgical device, in particular an implant as claimed, with an implant manufactured by using said method as claimed and with a method for fixing bone using said implant as claimed.

Definitions for currently used terms in the claims and the description:

General collection of three-dimensional bone quality data: a set of data including the entity of bone quality data analysed in the complete patient population, e.g. obtained from a variety of bone or bone portions.

Homologous sub-collection: the bone quality data of the N>2 homologous sub-collections is obtained from bone material of identical volume in identical anatomical positions of the patient population.

Categories: The patient population is divided in categories by applying the following criterions:

It is well known that nowadays surgeons do not consider all patients as belonging to the same category. For instance, osteoporotic and healthy individuals are considered as two different patient categories [Goldhahn J, Suhm N, Goldhahn S, Blauth M, Hanson B.; Influence of osteoporosis on fracture fixation-a systematic literature review; Osteoporos Int. 2008 June; 19(6):761-72. Review; and van Rietbergen B, Huiskes R, Eckstein F, Rueegsegger P.; Trabecular Bone Tissue Strains in the Healthy and Osteoporotic Human Femur; J. Bone Mineral Research, v. 18, N 10, p. 1781-1787, 2003]. The present method does not specify the criteria for patients' classification. The criteria defined to categorize the entire patient's population in subpopulations, should be medically and market driven. The method delivers a procedure to assess if the proposed categories are significantly different, if a different implant is required for each category, and how to design an optimized implant for the specific category.

Essential features but not limiting the chance of patients categorization are: age, health status, fracture pattern, bone mineral density, bone quality (microarchitecture, cortex/spongiosa ratio).

A patient is allotted to a particular category as follows:

The categorization should be medically and market driven, i.e. the surgeons and the companies will decide which patient is allotted to a particular class. The surgeons can be expected to potentially ask for a large number of categories and thus a large number of implants and the implant producer to restrict this number due to economical reason. Together with signalmen, health status and fracture pattern, information on bone quantity and quality are appropriate indexes for patient categorization. Currently, Dual Energy X-ray Absorptiometry (DXA) is the standard method to determine the osteoporotic state and to justify patient's treatment, e.g. with bisphosphonates. The present procedure is based on data collected with high-resolution peripheral Quantitative Computed Tomography (hr-pQCT), which provides, compared to DXA measurements, significantly more accurate and valuable information on bone microarchitecture (i.e. bone quality) and density. At the same time this technique is more time consuming and increases the X-ray dose for the patient, making the pQCT availability in hospitals significantly lower than DXA machines. Recent studies have demonstrated a good correlation between DXA and hr-pQCT in respect to bone density assessment [Grampp S, Lang P, Jergas M, Glüer CC, Mathur A, Engelke K, Genant H K; Assessment of the skeletal status by peripheral quantitative computed tomography of the forearm: short-term precision in vivo and comparison to dual X-ray absorptiometry. J. Bone Miner Res. 1995 October; 10(10)1566-76]. Based on these facts, it is believed that it will be possible to assess the relation between categorizations based both on DXA and on hr-pQCT. Once the relation will be demonstrated DXA measurements might also be used as an additional tool to allot a patient to a certain category.

To correctly and reproducibly position the implant on or in the patient's bone or virtually on or in the bones of the database the following procedure can be applied:

In the clinical setting the space available to position an implant is substantially limited by the given surgical access. Anatomically shaped implants limit even more the chances for positioning. Therefore, the surgical approach described in implants' manuals allows reproducible positioning of an implant. The present method is dependent on the surgeon's ability in positioning the implant at the right location, however, the present method allows to quantify the precision of this positioning and its effect on the regions investigated.

The surgeons follow the described technique for surgical accesses. These take into consideration anatomical landmarks and boundary conditions of the bone (e.g. musculoskeletal structures, vessels, nerves). The implant anatomical shape gives an additional restrain to the implant positioning helping the surgeon finding the right location.

Mechanical properties of bony structures: The mechanical properties of the bony structures (e.g. bone strength) depend on many factors. In the bone research/industrial community it is well accepted that bone mineral density and distribution as well as bone microarchitecture are the most important contributing factors. It is known that cut-out risk after fracture fixation depends on the load transfer between implant's anchoring elements and bone fragments. In vitro mechanical testing demonstrated a direct relationship between mechanical properties (e.g. bone strength and failure behaviour) and bone's macro- and microproperties (e.g. bone density, trabecular structure) [Hildebrand T, Ruegsegger P.; Quantification of bone microarchitecture with the structure model index. Comp. Meth. Biomech. Biomed. Eng. 1: 15-23, 1997. Ulrich D, van Rietbergen B, Laib A, Rüegsegger P.; The ability of three-dimensional structural indices to reflect mechanical aspects of trabecular bone. Bone 25 (1): 55-60, 1999. Gabet Y, Kohavi D, Voide R, Mueller T L, Müller R, Bab I.; Endosseous Implant Anchorage is Critically Dependent on Mechanostructural Determinants of Peri-Implant Bone Trabeculae. J Bone Miner Res. 2009 Aug. 4. Hernandez C J, Keaveny T M.; A biomechanical perspective on bone quality. Bone. 2006 December; 39(6):1173-81].

The most important parameters used to define trabecular bone structure are:
Trabecular Thickness
Trabecular Separation
Trabecular Number
Trabecular Bone Pattern Factor
Euler number, indicator of connectivity in a 3D structure
DA degree of anisotropy
SMI (structure model index) which defines the prevalent trabeculae shape
Mean polar moment of inertia which indicates the resistance to a rotation of a cross section about a chosen axis
Porosity High quality volumes/Low quality volumes: High quality volumes, namely those suitable for anchorage of a bone fixation element, are defined as those where, due to the combined effect of bone quality/quantity and loading pattern, the resulting stress accumulation is minimal.

Low quality volumes, namely those where the operator might wish to increase the implant purchase and/or to augment the physical properties of the bone structure, are those where, due to the combined effect of bone quality/quantity and loading pattern, the resulting stress is critical.

The definition of maximum and minimum, or low and high quality volumes, determined inside each category based on statistical analyses.

Optimal place/optimal direction: Includes the loading pattern as a factor helping to assess where the implant best purchases. The whole set of variables will be tested with computational and biomechanical models.

Additionally, the through hole in the implant should be easily accessible and should respect the local anatomy. For example, in the humerus the through hole can not start on the lateral bone surface, exit in the bicipital groove and enter again medially in the humerus. The boundary conditions given to the present algorithm will exclude those directions and find among the available directions those where the quality of the volumes is optimal. It is to be clarified that the algorithm leaves the chance to augment also in those areas where the implant has already good purchase, i.e. not only low quality for augmentation and high quality for better implant purchase.

Configuration of the through holes: For a given category of patients and implant, the method optimizes the combinations of all the available anchorage parts. The optimization is completed when the combination of the investigated high quality volumes results in the minimal stress accumulation taking in consideration all the anatomical, technical (superimposition of screws) and surgical limitations.

At the same time for a given category of patients and implant, the method optimizes the combinations of all the available through holes dedicated to aim low quality volumes.

The number of through holes dedicated to aim low quality volumes is set according to the optimized number of anchorage parts and to final optimization concerning the best stress shearing configuration between bone and implant, also taking in consideration all the anatomical, technical (superimposition of screws) and surgical limitations. According to patients categorization the combination of low and high quality volumes can be identical or not and it aims to create minimum bone defects and maximum fixation stability. The method determines the best combined configuration of the directions of the axes of any locking system optimised for any purpose on any medical implant dedicated to any specific category of patients.

The depth of the bore hole in the bone or in particular the depth of the location for the application of bone cement taken into account by the surgeon when implanting said surgical implant can be determined as follows: Nowadays surgeons use fluoroscopic images to assess how deep in the bone they drilled. The present method gives the surgeon the tool to find the direction of the weakest region. Actual or future imaging techniques can be used to assess the holes depth.

In a special embodiment of said method said optimal place and said optimal direction is defined by the position and extension of bone volumes where the stress accumulation resulting from a combination of bone quality and load pattern is minimal. The summarized stress accumulation for all through holes of the implant is the criterion for implant optimization, design and manufacture with regard to the position and direction of each through hole.

In another embodiment of said method said optimal place and said optimal direction is defined by taking into account the position and extension of augmented low quality volumes, preferably augmented by means of applying a bone cement. A new generation implant can be manufactured according to one or both the above optimization criteria, as in the following examples:

An existing implant can be optimized with angular stable holes allowing precise local augmentation.
The direction of the anchoring parts of an existing implant can be optimized according to the high quality volumes characteristics of a given category, by maintaining the existing positions of the through holes.
The direction of the anchoring parts of a new implant can be optimized according to the high quality volumes characteristics of a given category, defining new positions of the through holes in an existing implant shape or in a newly designed implant shape.
The direction of the anchoring parts of a new implant can be optimized according to the high quality volumes characteristics of a given category, defining new position of the through holes in an existing implant shape or in a newly designed implant shape and with angular stable holes allowing precise local augmentation.

In again another embodiment of said method said optimal place and said optimal direction is defined by additionally taking into account the accessibility of the through hole through the bone tissue.

In a further embodiment of said method said implant is a fixed angle implant. In fixed angle implants the directions of the anchoring parts are defined by the through holes. These are characterized by a mechanical locking method which allows consistently pre-drilling and inserting anchoring parts along the same through holes orientation.

In yet a further embodiment of said method high resolution bone quality data is used allowing the assessment of the bone micro architecture at a resolution smaller than or equal to 100 µm. To assess bone micro-architecture, which is relevant for implant optimization, high resolution CT is necessary. Clinical CT cannot deliver such information. The present method provides the assessment of the bone micro architecture via CT scans performed at a resolutions 100 µm (intra-trabecular space).

In a special embodiment of said surgical device, in particular implant said central axis has a direction that, respecting the anatomical restrains, allows following the best combination of purchase directions for all the implants anchorage elements.

In another embodiment of said surgical device, in particular implant the orientation of said central axis and the position of said through holes are defined according to a relative reference system.

In case of an implant configured as a bone plate said relative reference system is given by the center of three not aligned monocortical holes, drilled as anchorage for the implant fixation points. In case of an implant configured as an intramedullary nail said relative reference system is given by the coordinate system created by the center of the three non aligned monocortical holes, drilled as anchorage for the implant fixation points. In case of a general medical device said relative reference system is given by the coordinate system created by the center of the three non aligned points, used as anchorage for the device fixation points.

In still another embodiment of said surgical device, in particular implant said through hole is provided with coupling means for temporarily attaching an instrument.

In a further embodiment of said surgical device, in particular implant said through hole is designed as a fixed angle hole for receiving a bone fixation element at a fixed angle.

In yet a further embodiment of said surgical device, in particular implant said through hole (3) is designed as a variable angle hole for receiving a bone fixation element at a variable angle, said variable angle hole having a central axis (4) corresponding to said optimal direction (see FIG. 1). This configuration allows the advantage that the variability of the angle allows the surgeon to align the bone fixation element upon insertion to take into account e.g. anatomical differences.

According to a further aspect of the invention an assembly is provided which comprises the surgical device, in particular implant according to the invention and an aiming or drilling device attachable to said coupling means.

In accordance with another aspect, an assembly comprising the implant according to the invention and a bone replacement material source attachable to said coupling means is provided. A bone augmentation technique with any material can be applied. By means of said source, e.g. a syringe or cannula it is possible to introduce bone replacement material at the weakest region of the bone.

In a special embodiment of said method for fixing fractures bones the fracture is reduced in a first step before applying said implant.

In accordance with yet another aspect a method is provided for selecting an optimal implant out of said designed or optimized implants for each of said N>2 categories of patients.

A BRIEF DESCRIPTION OF THE DRAWINGS

A special embodiment of the invention will be described in the following by way of example and with reference to the accompanying drawings in which:

FIG. 4 illustrates a bone plate with bone fixation means inserted in the through holes;

Figure 1:
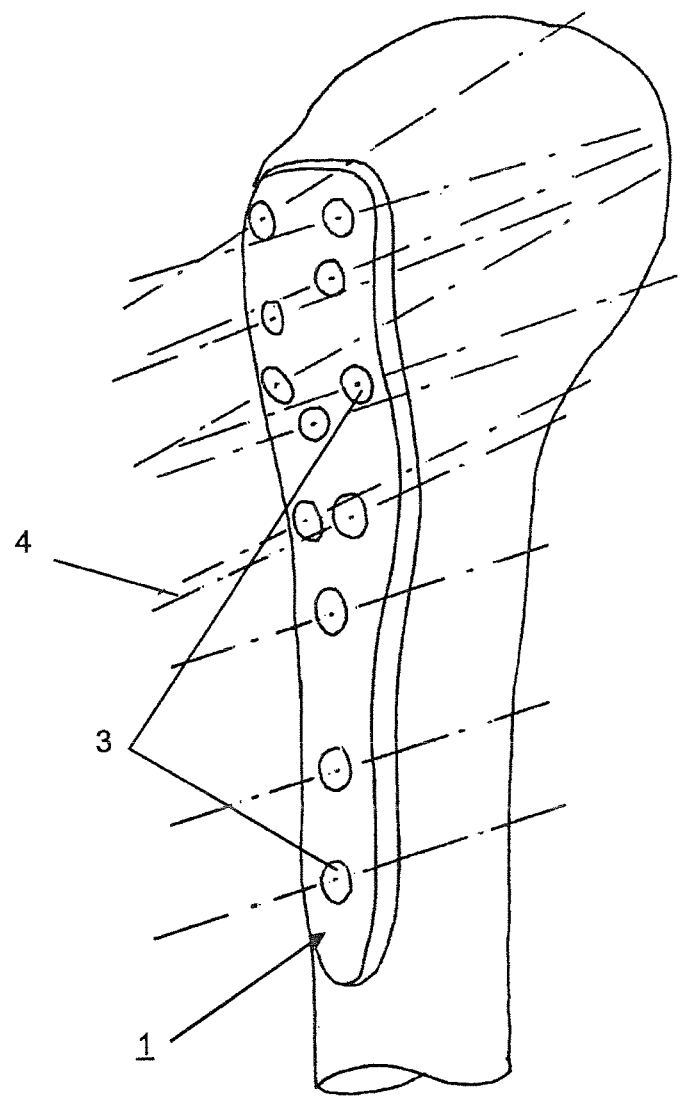
FIG. 1 illustrates a perspective view of an embodiment of the device according to the invention.

FIG. 5 schematically illustrates the assessment of bone quality along the direction where the anchoring elements purchase; and FIG. 6 illustrates a portion of a bone schematically depicting the process for the definition of optimal anchoring element directions according to the invention.

DETAILED DESCRIPTION OF THE INVENTION

FIGS. 1 to 6 illustrate an embodiment of the method according to the invention applied on the proximal humerus 6. The most common surgical implant 1 used to treat proximal humeral fractures is a plate. According to the fracture classification, this surgical device is applied on a region of the humerus where the bone is still solid. Surgical accesses available for surgeons to position this implants 1 are limited by the proximal humerus anatomy: vessels, nerves, precious musculoskeletal structures limit the fixation of the surgical implant 1 in determined and well described regions of the humerus. Bone fixation elements 2, e.g. locking screws 2 are used both to fix that plate and to reduce the fracture fragments allowing fracture repair.

Nowadays medical devices companies design the plate geometry following the mean shape of the lateral portion of the humerus. Differently, the direction of the screws used to fix the fragment is based mostly on surgeon's suggestion or experience. The high failure rate recorded in certain patients' categories suggest that the existing implant might not be optimized for all the patients' categories.

For a given category of patients and implant, the present method optimizes the combinations of all the available anchorage parts 5. The optimization is completed when the combination of the investigated high quality volumes results in the minimal stress accumulation taking in consideration all the anatomical, technical (superimposition of screws) and surgical limitations.

The optimization process according to the invention aims principally at helping the medical device company to define, according to the available surgical accesses and the loading pattern characteristic of a given area, the screws directions with the best purchase.

The present method includes consideration about the loading pattern of the region one implant 1 is optimized for.

The aim is finding the combination of screw direction such that the total stress in the bone is minimum for a given category.

The optimization process can be used for the following aims:
- Optimization of the directions of the locking screws for existing plates, so that the resulting screws combination delivers the best possible purchase.
- Novel plate design given the optimal screws directions in the humeral head, as assessed by high resolution scanning and matched with the surrounding anatomical structures.

Additionally, the procedure can be used to statistically assess directions or regions where the mechanical properties of the humerus are less advantageous. The surgeon will be able to use the same plate as aiming device to augment the bone mechanical properties in these specific areas.

The present method can be applied on any part of the body and implemented for the design of any kind of medical device aimed to fix any body tissue.

Figure 2:
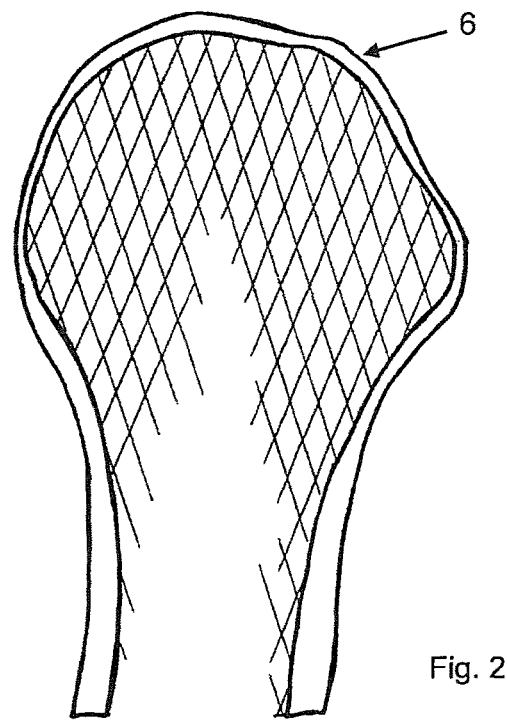
FIG. 2 illustrates a portion of a bone having a first trabecular bone distribution and mineral density.
Figure 3:
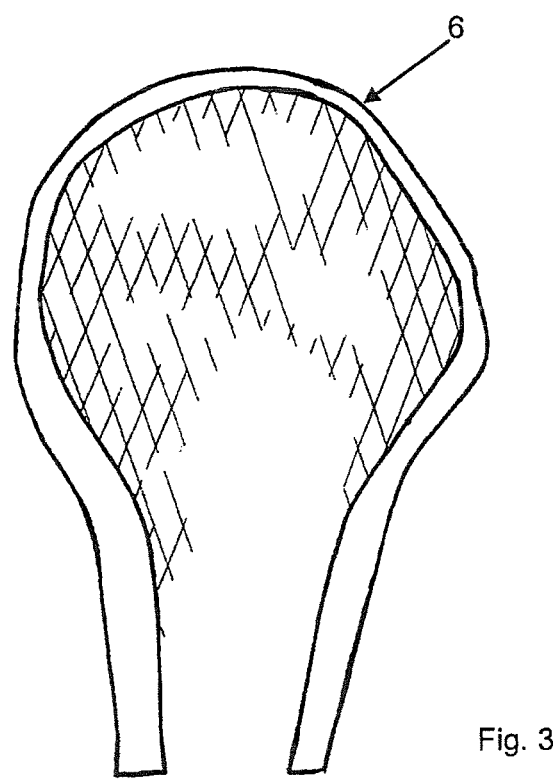
FIG. 3 illustrates a portion of a bone homologous the portion of the FIG. 2 having a second trabecular bone distribution and mineral density different from the first bone distribution and mineral density of FIG. 1.

The implant 1 is designed to be used with different categories of trauma patients having a different trabecular bone distribution and mineral density as illustrated in FIGS. 2 and 3.

FIGS. 4 and 5 illustrate the assessment of the bone quality along the directions 5 where the anchoring elements purchase in the bone 6. These are defined according to the existing implant design and standard positioning.

FIG. 6 illustrates a schematic depiction of the process for the definition of optimal anchoring element directions 5 based on peripheral Quantitative Computed Tomography (pQCT) of the bone 6.

The method according to the invention allows to build aiming tools for the ideal anchorage of devices. This method allows controlling of insertion points and devices directions. It is based on statistical shape analysis and/or individual information about the form and material properties of the body part requiring fixation, and on the loading pattern characteristic of the affected region. The number of access ports to each body region is limited by the anatomical characteristics of the surrounding tissues. According to the developed surgical techniques and the characteristics of the individuals they are dedicated to, implants and devices can have certain dimensions and can be positioned and fixed in determined regions. The geometrical properties of the devices are anatomically shaped based on CT reconstruction of the region where the fixation will be performed in order to facilitate the operator in positioning the device in the most adequate functional location. Devices dedicated to fix parts of the body can be subdivided in two regions: a first region anchored in the main part of the organ and a second one providing support to the displaceable part of the organ and connecting it to the main part of the organ. In these two regions "points for fixation" and "points for reduction" can be defined, i.e. points defining the positions and orientation of those parts of the device dedicated to fix it to the main part of the organ, and points defining the positions and orientation of those parts of the device dedicated to fix the displaceable part of the organ, respectively. The position of the points for fixation is always easily determined and, nowadays, does not affect the fixation outcome. On the other hand the positions of the points for reduction are, up to now, based exclusively on experience. The invention defines a method to assess the material properties of portions of the body part (later on cited as volumes) to fix, whose position and dimensions are completely defined starting from the "points for reduction". The positions of the points for reductions are uniquely defined by the reference system created using the point for fixation.

Knowing the positions of these points and the loading conditions, the method can be used for following purposes:
- to identify volumes of interest in a body part and retrieve information, from a bone database or a single individual, about their material properties (design of medical devices based on material properties mapping and loading conditions).
- to determine the ideal anchorage of devices (optimization of the direction of the parts used to reduce the body parts).
- to determine the ideal attachment points for augmentation (optimization of the direction of the parts used to augment the body parts if required).
- to determine the position of the best points for reduction on a device based on:
  - the ideal anchorage of devices (in example: optimization of the position of a hole in a given plate used to reduce the body parts).
  - the attachment points for augmentation (in example: optimization of the position of a hole in a given plate used as aiming tool to reach some body parts to augment).
- to change intraoperatively the direction of a given part of the fixation devices in order to aim it towards the ideal anchorage area for devices or to the ideal attachment points for augmentation.

For the loading pattern characteristic of a region, the ideal anchorages of devices are defined as the combination of those volumes and points where the material properties of the parts to fix are more beneficial for devices' anchorage (high quality volumes—high QV—even stress shearing). The attachment points for augmentation are defined as those directions and points where the material properties of the part to fix are disadvantageous (low quality volumes—low QV) and the operator might wish to increase the devices' purchase and/or to augment the physical properties of the structure.

While various descriptions of the present invention are described above, it should be understood that the various features can be used singly or in any combination thereof. The scope of the present invention is accordingly defined as set forth in the appended claims.

The invention claimed is:

1. A method for designing and/or optimizing and subsequently manufacturing a plurality of different implants configured for fixation to or in a bone by means of one or more bone fixation elements, the method comprising:
   providing a general collection of three-dimensional bone quality data obtained from a variety of different bone or bone portions analyzed in an investigated patient population;
   identifying three or more categories in the general collection containing homologous sub-collections of bone quality data obtained from bone material of identical volume in identical anatomical positions of the investigated patient population, wherein each of said homologous sub-collections of bone quality data is different;
   designing and/or optimizing the plurality of different implants, wherein each one of said plurality of different implants is designed and/or optimized for a different one of the three or more categories identified in the investigated patient population, wherein each one of said plurality of different implants has a surface configured to be placed adjacent to or in contact with the bone, wherein each one of said plurality of different implants is provided with one or more through holes for receiving the one or more bone fixation elements, wherein each of said one or more through holes has a central axis, wherein each of said one or more through holes is located at an optimal place and with an optimal direction of said central axis relative to a respective one of said plurality of different implants, wherein said optimal place and optimal direction are chosen so as to obtain an optimal anchorage of one of said one or more bone fixation elements in the bone when introduced through one of said one or more through holes; and manufacturing each of the designed and/or optimized plurality of different implants.

2. The method according to claim 1, wherein said optimal place and said optimal direction are defined by a position and extension of a bone volume where stress accumulation resulting from a combination of bone quality and load pattern is minimal.

3. The method according to claim 2, wherein said optimal place and said optimal direction are defined by taking into account positions and extensions of augmented low quality volumes.

4. The method according to claim 1, wherein said optimal place and said optimal direction are defined by additionally taking into account accessibility of the respective one of the one or more through holes through the bone.

5. The method according to claim 1, wherein said implant is a fixed angle implant.

6. The method according to claim 1, wherein the bone quality data is high resolution, allowing assessment of microarchitecture of the bone at a resolution less than or equal to 100 µm.

7. An implant manufactured according to the method of claim 1.

8. The implant according to claim 7, wherein said central axis of each of the one or more through holes has a direction that, respecting anatomical restraints, allows the best combination of directions for the respective bone fixation elements to obtain the optimal anchorages.

9. The implant according to claim 7, wherein an orientation of said central axis and the optimal place of each of said one or more through holes are defined according to a relative reference system.

10. The implant according to claim 9, wherein the implant is a bone plate and said relative reference system is given by a center of three not aligned monocortical holes, drilled as anchorage for implant fixation points.

11. The implant according to claim 9, wherein the implant is an intramedullary nail and said relative reference system is given by a coordinate system created by a center of three not aligned monocortical holes, drilled as anchorage for implant fixation points.

12. The implant according to claim 9, wherein the implant is a general medical device and said relative reference system is given by a coordinate system created by a center of three not aligned points, used as anchorage for device fixation points.

13. The implant according to claim 7, wherein at least one of said one or more through holes is provided with coupling means for temporarily attaching an instrument.

14. An assembly comprising the implant according to claim 13 and an aiming or drilling device attachable to said coupling means.

15. An assembly comprising the implant according to claim 13 and a bone replacement material source attachable to said coupling means.

16. The implant according to claim 7, wherein said one or more through holes are fixed angle holes for receiving the bone fixation element at a fixed angle.

17. The implant according to claim 7, wherein said one or more through holes are variable angle holes for receiving the bone fixation element at a respective variable angle, said central axis of each of the variable angle holes corresponding to said respective optimal direction.

18. A method for fixing bones of a human or animal body, comprising providing the implant according to claim 7 and applying the implant to fix the bones.

19. The method according to claim 18, wherein the bones fixed by the method are fractured bones, and wherein in a first step the fracture is reduced before applying said implant.

20. A method for fixing a bone in a patient, the method comprising:
providing a plurality of implants designed and/or optimized and subsequently manufactured according to claim 1, wherein each of said plurality of implants is configured for implantation into one of the three or more categories in the investigated patient population containing homologous sub-collections of bone quality data;
selecting an optimal implant from said plurality of implants for implantation in the patient based on which one of the three or more categories in the investigated patient population containing homologous sub-collections of bone quality data matches the patient's bone quality data; and
fixing the optimal implant to the bone using one or more bone fixation elements inserted through one or more respective through holes provided in the optimal implant.

* * * * *